US007731939B2

(12) United States Patent
Miller et al.

(10) Patent No.: US 7,731,939 B2
(45) Date of Patent: Jun. 8, 2010

(54) VACCINE COMPOSITIONS AND ADJUVANT

(75) Inventors: Lowell A. Miller, Greeley, CO (US); Jack C. Rhyan, Fort Collins, CO (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/893,464

(22) Filed: Aug. 16, 2007

(65) Prior Publication Data

US 2008/0233153 A1 Sep. 25, 2008

Related U.S. Application Data

(60) Continuation of application No. 11/224,569, filed on Sep. 12, 2005, now abandoned, which is a continuation of application No. 10/833,903, filed on Apr. 28, 2004, now abandoned, which is a division of application No. 10/251,107, filed on Sep. 20, 2002, now abandoned.

(51) Int. Cl.

| | |
|---|---|
| *A61K 49/00* | (2006.01) |
| *A61K 39/04* | (2006.01) |
| *C12N 11/00* | (2006.01) |

(52) U.S. Cl. ...................... 424/9.2; 424/9.1; 424/184.1; 424/185.1; 424/248.1; 435/174

(58) Field of Classification Search ................. 424/9.1, 424/9.2, 184.1, 185.1, 248.1; 435/174
See application file for complete search history.

(56) References Cited

OTHER PUBLICATIONS

Kondo, Y. et al. "Elevated adjuvanticity of non-acid-fast Mycobacteria". Infection and Immunity, vol. 26, No. 1, pp. 19-24, Oct. 1979.*
Miller, L.A., et al. "Immunocontraception of white-tailed deer with GnRH vaccine", American Journal of Reproductive Immunology, vol. 44, pp. 266-274, 2000.*

* cited by examiner

*Primary Examiner*—Rodney P. Swartz
(74) *Attorney, Agent, or Firm*—John Fado; Randall E. Deck; Lesley Shaw

(57) ABSTRACT

The immune response of an animal to a target immunogen may be enhanced by use of a novel adjuvant which includes low concentrations of killed cells of *Mycobacterium avium* subspecies *avium* in combination with mineral oil. The adjuvant may be used in vaccine compositions for the immunization of an animal against any target immunogen, and is particularly preferred for use with immunocontraceptive vaccines such as GnRH and PZP immunocontraceptive vaccines.

11 Claims, 4 Drawing Sheets

VACCINE COMPOSITIONS AND ADJUVANT

BACKGROUND OF THE INVENTION

1. Field of the Invention

The invention relates to novel vaccine compositions, including immunocontraceptive vaccines, and particularly to novel adjuvants for use therein.

2. Description of the Prior Art

Gonadotropin releasing hormone ("GnRH", also known as Luteinizing Hormone Releasing Hormone, or "LHRH"), has long been recognized as being of central importance to the regulation of fertility in animals. GnRH is a decapeptide which has the same amino acid sequence, i.e., pGlu-His-Trp-Ser-Tyr-Gly-Leu-Arg-Pro-GlyNH$_2$ (SEQ ID NO. 1) in all mammals. Closely related GnRH compounds have also been identified in other non-mammals, including fowl, and receptors for GnRH have been identified in reptiles and amphibians. In males and females, GnRH is released from the hypothalamus into the bloodstream and travels via the blood to the pituitary, where it induces the release of the gonadotropins, luteinizing hormone (LH) and follicle stimulating hormone (FSH). These two gonadotropins, in turn, act upon the gonads, inducing steroidogenesis and gametogenesis. In growing male animals, the gonadotropins stimulate the development of the testes and the synthesis of testicular steroids. In the growing female animal the development of the ovaries is stimulated and therein follicle development, synthesis of ovarian steroids and ovulation. Steroids released from the gonads into the circulation also act upon various other tissues.

In recent years, GnRH neutralization has been used as an effective means of contraception in a variety of animals. Fraser described that the gonadotropin hormonal cascade can be halted by neutralization of the biological activity of GnRH (Physiological Effects of Antibody to Luteinizing Hormone Releasing Hormone. In: Physiological Effects of Immunity Against Reproductive Hormones, Edwards and Johnson, Eds. Cambridge University Press, 1976). As a consequence of GnRH neutralization, the gonadotropins and gonadal steroids are not released into the blood, interrupting the hormonal regulation of fertility and ceasing gametogenesis. In addition to the use of immunization against GnRH for animal sterilization to prevent breeding, the immunization has also been suggested for the treatment of aggressiveness in male animals such as dogs and bulls, chemical castration of male animals for slaughter, prevention of heat in female animals, and prevention of restlessness in male animals being fattened for slaughter, and reduction of boar taint in the meat of pigs raised for slaughter.

Neutralization of GnRH has also been employed for the treatment of a number of other diseases. A number of important diseases, including breast cancer, uterine and other gynecological cancers, endometriosis, uterine fibroids, prostate cancer, and benign prostatic hypertrophy, are also affected by gonadotropins and gonadal steroid hormones. Neutralization of the patient's GnRH effectively eliminates the gonadal steroids that induce and stimulate these diseases. See McLachlan et al., 1986, British Journal of Obstetrics and Gynecology, 93:431-454; Conn and Crowley, 1991, New England Journal of Medicine, 324:93-103; Filicori and Flamigni, 1988, Drugs, 35:63-82.

GnRH neutralization has been typically achieved by the induction or introduction of anti-GnRH antibodies in the subject animal or patient. These antibodies may be induced by active immunization with GnRH immunogens, or by passive immunization by administering anti-GnRH antibodies (Fraser, 1976, ibid). Antibodies to GnRH produce infertility by binding to circulating endogenous GnRH, precluding the GnRH from binding to its pituitary receptor and thereby interfering with its ability to release FSH and LH. The severe reduction or absence of these hormones leads to atrophy of the gonads and concomitant infertility in both sexes as described above.

Despite these advantages, active immunization against GnRH has not been widely practiced due to deficiencies associated with the GnRH vaccines. The prior art anti-GnRH vaccines have typically lacked the potency necessary to effect long-term contraception in a single dose. In fact, immunocontraception has traditionally required at least two doses, a prime and a boost, for long-term efficacy. The prime dose prepares the immune system for repeat antigen exposure and provides only a short term response. The subsequent boost immunization can result in an immune response which can be maintained for a period of months to years. In addition to the GnRH immunogen, an adjuvant is a necessary component of any vaccine intended for long-lasting immunocontraception.

At present, Freund's complete adjuvant (FCA) is the only adjuvant that has provided high and long-lasting immunocontraceptive responses. Although many other adjuvants have been developed, none have been able to achieve the high antibody titers obtained using Freund's complete adjuvant. Freund's complete adjuvant includes a emulsion of killed bacteria of *Mycobacterium tuberculosis* or *M. butyricum* (also known as *M. smegmatis*) in mineral oil with a surfactant.

Despite the efficacy achieved with Freund's complete adjuvant, numerous concerns have been raised over its use in animals, and particularly in animals raised for human consumption. One primary concern has been the potential for false-positive TB skin tests in an animal which has been injected with FCA containing killed *M. tuberculosis* (Tizard, 1977, An Introduction to Veterinary Immunology, CRC Press, Boca Raton, Fla.). Other concerns over the use of FCA have included fears that it may be carcinogenic and that it may cause intense cell-mediated immune responses which produce lesions at the site of injection.

SUMMARY OF THE INVENTION

We have now invented improved methods and compositions for vaccinating animals. In accordance with this invention, the immune response of an animal to a target immunogen may be enhanced by use of a novel adjuvant which includes low concentrations of killed cells of *Mycobacterium avium* subspecies *avium* in combination with mineral oil. While the adjuvant may be used in vaccine compositions for the immunization of an animal against any target immunogen, it is particularly preferred for use with immunocontraceptive vaccines such as gonadotropin releasing hormone (GnRH) and porcine zona pellucida (PZP) immunocontraceptive vaccines.

In accordance with this discovery, it is an object of this invention to provide vaccine compositions having a novel adjuvant.

Another object of this invention is to provide a novel adjuvant for use with vaccine compositions which provides superior enhancement of immune response to the target immunogen but which produces substantially no inflammation at the site of injection.

Still another object of this invention is to provide novel vaccine compositions for the immunocontraception of animals.

Yet another object of this invention is to provide novel contraceptive vaccine compositions which are effective for long periods of time with only a single shot.

Other objects and advantages of this invention will become readily apparent from the ensuing description.

DETAILED DESCRIPTION OF THE INVENTION

Figure 1:
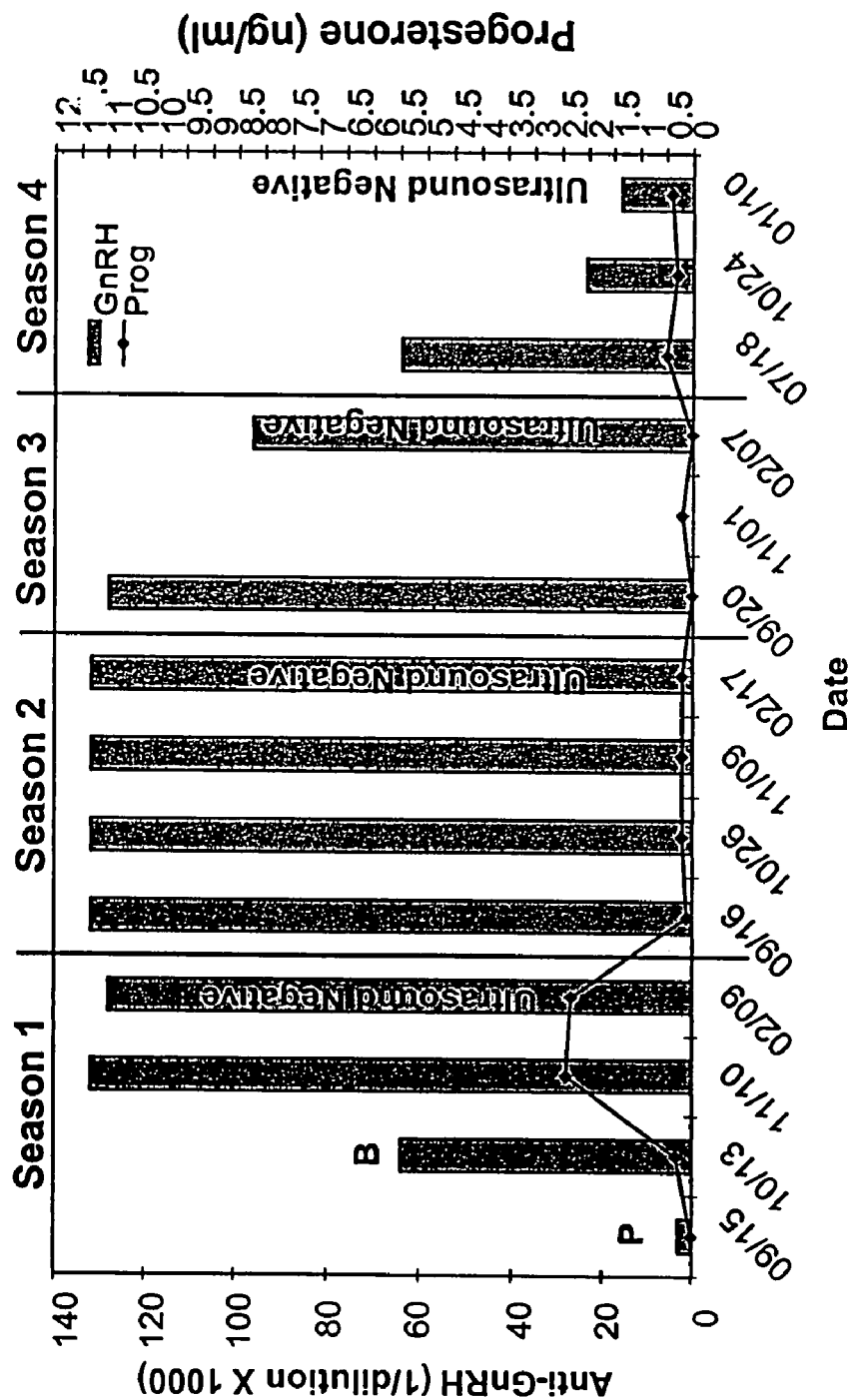
FIG. 1 shows the results of the first study of Example 3 over four consecutive seasons with deer immunized with a prime dose followed by a second, boost dose.

In accordance with this invention we have developed novel adjuvants for use in the active immunization of animals. Traditionally, vaccines are prepared using a combination of the an immunologically effective amount of an immunogen of interest together with an adjuvant effective for enhancing the immune response of the animal against the immunogen. We have unexpectedly discovered that compositions of mineral oil with low concentrations of killed cells of *Mycobacterium avium* subspecies *avium* provide effective enhancement of immune responses and thus are effective for use as adjuvants. Moreover, this adjuvant provides enhanced immune responses which exhibit high, long-lasting antibody titers to the immunogen, even after administration of only a single dose of the vaccine.

As used herein *Mycobacterium avium* subspecies *avium* refers to the recognized species *M. avium* subspecies *avium*, the characteristics of which are described by Thorel et al. (1990, International Journal of Systematic Bacteriology, 40:254-260, the contents of which are incorporated by reference herein) and the type strain of which has been deposited at the American Type Culture Collection, Manassas, Va., USA, as deposit accession number ATCC 25291. In contrast, as used herein *Mycobacterium avium* does not refer to the *M. avium* "complex" which has been used in the art to collectively include both of the two subspecies *M. avium* subsp. *avium* and *M. avium* subsp. *paratuberculosis*.

Without wishing to be bound by theory, it is believed that the high efficacy of the *M. avium* subsp. *avium* containing adjuvant is due to the nearly ubiquitous presence of this microorganism in nature. Indeed, most living animals, including humans, have been exposed to *M. avium* subsp. *avium* in the environment. We believe that because most animals have been naturally exposed to the microorganism, when they are initially injected with the immunogen plus adjuvant the immune response is enhanced by a specific response to the *M. avium* subsp. *avium* which is similar to that of a booster injection. The initial injection with the adjuvant of this invention therefore elicits an immune response which is usually seen only after a boost injection of other adjuvants.

The particular strain of *M. avium* subsp. *avium* used in the preparation of the adjuvant is not critical. *M. avium* subsp. *avium* suitable for use in the adjuvant may be obtained from a variety of sources including known substantially pure strains or it may be isolated from natural sources such as fowl or other animals using conventional techniques. For commercial production of the adjuvant, large quantities of cells of the microorganism are preferably prepared by culture of the selected strain. Alternatively, killed cells may be obtained directly from commercial sources, such as the Johne's disease vaccine, MYCOPAR (manufactured by Fort Dodge Animal Health, Overland Park, Kans., USA, and distributed by Solvay Animal Health, Mendota Heights, Minn., USA), which consists of killed cells *M. avium* subsp. *avium* strain 18.

Propagation of the microorganism for preparation of the adjuvant may be accomplished by culture under any conventional conditions and on media which promote its growth. Although a variety of conventional solid and liquid media may be suitable for use herein, growth in liquid culture is particularly preferred for large scale production. Without being limited thereto, Middlebrook broth is preferred. The microorganism will grow over wide temperature ranges, although growth between 34-38° C. is typically preferred? Once a sufficiently heavy growth of the microorganism has been obtained, usually in about 10-25 days, the cells may be recovered and separated from the culture medium using techniques conventional in the art, such as by centrifugation or filtration. Following separation, the cells may be further washed to remove contamination by extraneous microbial products or culture media components.

Following their propagation and recovery, cells of *M. avium* subsp. *avium* are subjected to chemical and/or physical treatment effective to kill (i.e., inactivate) the cells. An effective treatment for killing the cells is defined herein as that which kills 99.9% or more of the viable cells, without lysing the cells and while retaining the ability of the cells to elicit an antibody response in the animal. Thus, the treatment should not substantially alter the specificity of the cell surface antigens on the killed cells relative to the untreated cells. While treatments killing 100% of all viable cells would typically be preferred, particularly for any applications involving treatment of humans, the skilled practitioner will recognize 100% cell death may not be critical in veterinary applications, particularly in view of the ubiquitous nature of the microorganism. In the preferred embodiment, killed, intact *M. avium* subsp. *avium* are prepared by treatment of the viable cells with alcohol, particularly an aliphatic alcohol such as ethanol or isopropyl alcohol. Alternatively, the cells may be killed by UV irradiation such as described by Purdy et al. (U.S. Pat. No. 6,303,130) for the preparation of *Pasteurella haemolytica* bacterins. It is also envisioned that a variety of other techniques have been described for the preparation of killed cell vaccines (i.e., bacterins) are also suitable for use herein, and include but are not limited to treatment with phenol, tricresol, formalin, formaldehyde, acetone, merthiolate, and moderate heat at temperatures which would not induce protein denaturation (e.g., 56° C. for 1 hour). Treatment times and conditions will of course vary with the particular method selected and may be readily determined by routine testing.

Adjuvant formulations are prepared by combining the killed cells with mineral oil, which is also used in the preparation of the well-known Freund's adjuvant, and an optional surfactant or emulsifier. Inclusion of a surfactant is indicated when either or both of the *M. avium* subsp. *avium* killed cells or the immunogen of interest are in an aqueous solution or suspension. The particular surfactant used is not critical, and a variety of surfactants are suitable for use herein for emulsifying any aqueous components. Although mannide monooleate is a generally preferred surfactant, examples of alternative surfactants which may also be used include but are not limited to polyoxyethylene ethers (or octoxynols) such as lauryl, cetyl, oleyl, stearyl, and tridecyl polyoxyethylene ethers; polyoxyethylene sorbitan-fatty acid esters (commonly sold under the trade name TWEEN by ICI Americas Incorporated, Wilmington, Del.), such as polyoxyethylene (20)sorbitan monolaurate (TWEEN 20), polyoxyethylene (60)sorbitan monolaurate (TWEEN 60); polyoxyethylene ethers such as TRITON X-100, X-102, X-165, and X-305; fatty acid diethanolamides such as isostearic acid DEA, lauric acid DEA, capric acid DEA, linoleic acid DEA, myristic acid DEA, oleic acid DEA, and stearic acid DEA; fatty acid monoethanolamides such as coconut fatty acid monoethanolamide; fatty acid monisopropanolamides such as oleic acid monoisopropanolamide and lauric acid monoisopropanolamide; alkyl amine oxides such as N-cocodimethylamine oxide, N-lauryl dimethylamine oxide, N-myristyl dimethylamine oxide, and N-stearyl dimethylamine oxide; N-acyl amine oxides such as N-cocoamidopropyl dimethylamine oxide and N-tallowamidopropyl dimethylamine oxide; and N-alkoxyalkyl amine oxides such as bis(2-hydroxyethyl) $C_{12}$-$C_{15}$ alkoxy-propylamine oxide. The amount of the surfactant, if used, is not critical but should be sufficient to emulsify any aqueous components. Consequently, the relative amounts of mineral oil to surfactant in the adjuvant will typically be between about 85:15 and about 100:0, by weight, respectively. In the preferred embodiment, the ratio of mineral oil to surfactant may vary between about 85:15 to 95:5, respectively, and in particularly preferred embodiment is about 95:5.

In contrast to the mineral oil and surfactant, the amount of killed cells of *M. avium* subsp. *avium* is critical. The objective of the adjuvant of this invention coincides with the well-established use of adjuvants in the active immunization art, which is to enhance the immune response of an animal to immunization with a target immunogen, specifically, to enhance the production of antibodies against the target immunogen. Thus, the adjuvant is administered in a vaccine composition which includes a target immunogen of interest, wherein the target immunogen is itself present in an immunologically effective amount. As used throughout the art and herein, an immunologically effective amount of the target immunogen is defined as that amount which will elicit production of antibody by the subject animal against the immunogen.

Consequently, in accordance with the instant invention, the absolute amount of the killed cells of *M. avium* subsp. *avium* and their concentration in the final vaccine composition (which includes the target immunogen) which is administered to the subject animal are selected to provide an effective enhancement (i.e., increase) of the production of the antibody against the target immunogen as compared to a control animal (treated with a vaccine composition lacking the adjuvant). However, the amount of the killed cells of *M. avium* subsp. *avium* in the vaccine composition should not be so high that it would elicit a substantial T cell-mediated delayed hypersensitivity response (i.e., a Type IV response) by the animal to the *M. avium* subsp. *avium* if the adjuvant were administered alone without immunogen. A substantial T cell-mediated delayed hypersensitivity response to *M. avium* subsp. *avium* is defined herein as a skin reaction at the site of injection of the vaccine which is visible to the naked eye. Although the administration of the inventive adjuvant may produce a reaction on a microscopic level which may be seen upon microscopic examination of biopsy material, no granuloma at the site of injection will be visible to the naked eye. Thus, the amount of the killed cells used in the vaccine will be much less than that which might be typically used for a target immunogen. The precise effective amount of the killed cells used in the vaccine composition may vary somewhat with the particular target animal and its size, and the stage of the vaccination (initial or single dose, or second or boost dose) and may be determined by the practitioner in the art by routine experimentation. Without being limited thereto, the concentration of said killed cells of *M. avium* subsp. *avium* in the vaccine formulation administered to a subject animal will typically vary between about 50 µg per ml and about 400 µg per ml, measured as the dry weight of said killed cells per ml of the vaccine composition. Within this range, the initial dose of vaccine formulations administered to an animal in either a single or multiple dose program will generally have a greater amount of killed cells of *M. avium* subsp. *avium*, than boost doses. Further, as a practical matter, the volume of vaccine compositions which may be administered to animals parenterally by injection is relatively small, no greater than about 1 ml for all but very large animals such as elephants or whales. Consequently, the volume of adjuvant and hence the amount of killed cells of *M. avium* subspecies *avium* in the vaccine composition is also limited. Thus, in a preferred embodiment for the treatment of animals weighing less than about 2,000 pounds (i.e. animals except the above-mentioned very large animals), the vaccine composition will typically contain more than or equal to about 50 µg and less than or equal to about 400 µg of killed cells of *M. avium* subsp. *avium* by weight, and particularly more than or equal to about 50 µg and less than or equal to about 200 µg of the killed cells by weight.

The manner of formulating the adjuvant and immunogen containing preparation may vary with the phase of the immunogen preparation, the concentration of the immunogen in the preparation, its solubility, and the carrier used for the immunogen preparation, if present. For instance, without being limited thereto, when formulated with aqueous phase solutions or suspensions of an immunogen, the adjuvant and immunogen preparation are preferably formulated in approximately equal volumes, vigorously agitated to form an emulsion, and finally stiffened by passage through a needle as is conventional in the art. Conversely, lyophilized immunogen preparations may be mixed directly with the adjuvant without the need for emulsification. Immunogen preparations in oil miscible carriers may also be simply mixed with adjuvant, again preferably in approximately equal volumes.

The *M. avium* subsp. *avium* containing adjuvants of the invention may be used in combination with a variety of known immunogens or antigens used for active immunization of animals by parenteral injection to elicit production of antibodies reactive with the immunogen. The adjuvants are preferred for use with GnRH, and particularly with GnRH or porcine zona pellucida (PZP) immunocontraceptive vaccines. However, it is also envisioned that the adjuvants may be used with virtually any other known immunogen of interest other than *M. avium* (such as Johne's disease vaccine). Thus, the adjuvant may be used with pathogenic microorganisms (living, attenuated, or killed) or biological molecules including toxoids, polysaccharides, proteins, peptides, or microbial subunits, which further include relatively large molecules which are themselves antigenic in a target animal as well as smaller haptens or self molecules conjugated to immunogenic carriers. Examples of immunogens used in vaccination programs which may be used with the adjuvants of the invention include but are not limited to *Pasteurella haemolytica, Vibrio cholera, Corynebacterium diptheriae* toxoid, Hepatitis B viral antigen, Influenza virus, Measles virus, Meningococcal polysaccharide, Mumps virus, killed cells of *Bordetella pertusis, Streptococcus pneumoniae* (pneumococcus) polysaccharide, Polio viruses, Rabies virus, Rubella virus, poxviruses such as Vaccinia virus, *Clostridium tetani* toxoid, *Mycobacterium bovis*, killed cells of *Salmonella typhi*, and Yellow fever virus.

In a particularly preferred embodiment, the adjuvant is formulated with a GnRH or GnRH immunogenic mimic containing vaccine for inducing production of anti-GnRH antibody in an animal and thereby effecting one or more responses ranging from contraception in males and/or females, reducing aggressive behavior in male animals, chemical castration, control or prevention of estrus or heat, prevention of restlessness in animals prior to slaughter, reduction of boar taint in the meat of pigs raised for slaughter, and treatment of diseases as is known in the art.

While GnRH may be used in the immunogen preparation, a variety of GnRH immunogenic analogs have also been described which are suitable for use herein. As noted hereinabove, GnRH is a small decapeptide having the amino acid sequence: pGlu-His-Trp-Ser-Tyr-Gly-Leu-Arg-Pro-Gly-NH$_2$ (Seq. ID No. 1). Throughout this description, the amino acid sequences conform with conventional practice with the amino terminal amino acid on the left and the carboxy terminal amino acid to the right. As defined herein, immunogenic analogs of GnRH include compounds containing a substitution, deletion, or insertion of between one and five amino acid residues in the above-mentioned GnRH amino acid sequence, as well as dimers or polymers thereof, which compound retains the ability to induce or stimulate the production in a subject animal of antibodies which bind (i.e., cross-react) to GnRH. The GnRH analog will preferably retain at least five consecutive amino acids from the GnRH decapeptide. The substitutions and insertions can be accomplished with natural or non-natural amino acids, and substitutions are preferably conservative substitutions made with amino acids which maintain substantially the same charge and hydrophobicity as the original amino acid. Moreover, the analog may itself be immunogenic or it may be coupled to an immunogenic carrier such as described hereinbelow.

Immunogenic analogs of GnRH which are suitable for use herein have been described, for example, in Meleon (U.S. Pat. Nos. 5,484,592 and 6,284,733), Mia (U.S. Pat. No. 4,608, 251), Ladd et al. (U.S. Pat. No. 5,759,551), Hoskinson et al. (published PCT application WO8805308), and Russell-Jones et al. (U.S. Pat. No. 5,403,586) the contents of each of which are incorporated by reference herein. Thus, suitable GnRH analogs include but are not limited to GnRH peptides wherein the Gly at position 6 of the GNRH decapeptide has been replaced by a dextrorotary (D)-amino acid such as D-trp, D-glu, or D-lys (Seq. ID No. 2, 3, and 4, respectively); GnRH peptides wherein the p-Glu at position 1 of the GnRH decapeptide has been replaced by a Glu, His, or Pro (Seq. ID No. 5, 6, and 7, respectively); any continuous 5, 6, 7, 8, or 9 amino acid fragment of the GnRH decapeptide, such as pGlu-His-Trp-Ser-Tyr, pGlu-His-Trp-Ser-Tyr-Gly, pGlu-His-Trp-Ser-Tyr-Gly-Leu, His-Trp-Ser-Tyr-Gly-Leu-Arg, Trp-Ser-Tyr-Gly-Leu-Arg, Ser-Tyr-Gly-Leu-Arg-Pro-Gly-NH$_2$, and Tyr-Gly-Leu-Arg-Pro-Gly-NH$_2$ (Seq. ID Nos. 9-15, respectively); naturally occurring chicken GnRH II, pGlu-His-Trp-Ser-His-Gly-Trp-Tyr-Pro-Gly-NH$_2$ (Seq. ID No. 16); naturally occurring salmon GnRH, pGlu-His-Trp-Ser-Tyr-Gly-Trp-Leu-Pro-Gly-NH$_2$ (Seq. ID No. 17); the nona- or decapeptide (Cys)-Lys-Trp-Ser-Tyr-Gly-Leu-Arg-Pro-Gly-NH$_2$, wherein the amino terminal Cys is optional (Seq. ID Nos. 18 and 19, respectively) or a dimer of the decapeptide wherein the amino terminal Cys are coupled to one another (Seq. ID No. 20); a polymer of two or more decapeptides in tandem of the formula Z$^1$-Glx-His-Trp$^1$-Ser-Tyr-Gly-Leu-Arg-Pro[-Gly-X-Gln-His-Trp-Ser-Tyr-Gly-Leu-Arg-Pro]$_n$-Gly-Z$^2$ wherein n is an integer greater than or equal to 1, X is a direct bond or a spacer, Z$^1$-Glx is pGlu or Gln having an amino acid tail attached thereto for coupling to a carrier protein, and Gly-Z$^2$ is Gly-NH$_2$ or Gly having an amino acid tail attached thereto for coupling to a carrier protein (Seq. ID No. 21); and a peptide having the sequence pGlu-His-Trp-Ser-Tyr-Y-Leu-Arg-Pro-Gly-Gln-His-Trp-Ser-Tyr-Y-Leu-Arg-Pro-Gly-Cys wherein Y is independently Gly or a D-amino acid which may optionally contain an amino acid side chain attached thereto for coupling to a carrier protein (Seq. ID No. 22) or a dimer thereof.

While the GnRH may be isolated from natural sources, for practical purposes GnRH or and its analogs may be synthesized by a variety of conventional methods Such techniques include but are not limited to methods well known to those skilled in the art of peptide synthesis, e.g., solution phase synthesis [see Finn and Hoffman, In "Proteins," Vol. 2, 3rd Ed., H. Neurath and R. L. Hill (eds.), Academic Press, New York, pp. 105-253 (1976)], or solid phase synthesis [see Barany and Merrifield, In "The Peptides," Vol. 2, E. Gross and J. Meienhofer (eds.), Academic Press, New York, pp. 3-284 (1979)], or stepwise solid phase synthesis as reported by Merrifield [J. Am. Chem. Soc. 85: 2149-2154 (1963)], the contents of each of which are incorporated herein by reference.

Because GnRH is a small, self-molecule it should be conjugated directly or indirectly to an immunogenic carrier in order to increase the immune response to the peptide. A plurality carriers and carrier coupling techniques have been previously described for GnRH or its analogs and are also suitable for use herein. See for example, Meleon, Mia, Ladd et al., Hoskinson et al., and Russell-Jones et al. mentioned above. However, in a preferred embodiment, GnRH or an analog thereof is conjugated to immunogenic mollusk hemocyanin carrier protein, directly or indirectly through the C-terminal end of the GnRH or analog. Suitable immunogenic mollusk hemocyanin proteins include *Concholepas concholepas* hemocyanin protein, Keyhole Limpet (*Megathura crenulate*) hemocyanin protein (KLH), Horseshoe crab (*Limulus polyphemus*) hemocyanin protein, and Abalone (*Haliotis tuberculata*) hemocyanin protein, with KLH and *Concholepas concholepas* hemocyanin protein being preferred.

Conjugation of GnRH or its analog to the mollusk hemocyanin protein is preferably conducted using a cross-linking agent to allow a large number of GnRH or analog molecules (i.e., 200 or more) to be coupled to a single carrier protein molecule, effectively covering its outer surface with consistently aligned epitopes of the GnRH displaying the same basic conformation. To ensure this consistent alignment, the GnRH (or its analog) is coupled through its C-terminal end to the N-terminal end of the carrier protein through a bifunctional cross-linking agent. In a particularly preferred embodiment, the GnRH/carrier conjugate may be shown by the formula:

$$(X\text{-}A_m\text{-}B\text{-}L)_n\text{-}R \qquad (I)$$

wherein X is GnRH or a GnRH immunogenic analog, A is an optional amino acid spacer such as Gly, m is an integer greater than or equal to 0, B is an amino mercaptan, R is an intact immunogenic mollusk hemocyanin protein, L is a bifunctional crosslinking agent effective for simultaneously binding to the thiol of the mercaptan and to free amine moieties of the immunogenic mollusk hemocyanin protein, and n is an integer greater than or equal to about 200. A variety of amino mercaptans may be used, provided that it possesses a free amino moiety for binding to the C-terminal end of X (or A if present) and a free thiol moiety for binding to the bifunctional crosslinking agent, although cysteine is preferred. Preferred bifunctional crosslinking agents include succinimidyl-4-(N-maleimidomethyl)cyclohexane-1-carboxylate (SMCC) or sulfo-SMCC (s-SMCC), either of which form a maleimide-activated carrier protein. Other crosslinking agents suitable for conjugating the carrier protein and GnRH through the thiol group of the amino mercaptan include but are not limited to the organic solvent soluble agents Succinimidyl 4-(p-maleimidophenyl)-butyrate (SMPB), -[(γ-Maleimidobutyryl)oxy]succinimide ester (GMBS), -Succinimidyl[4-iodoacetyl]-aminobenzoate (SIAB), and m-Maleimidobenzyl-N-hydroxysuccinimide ester (MBS), or their corresponding water soluble sulfonated forms sulfo-SMPB (s-SMPB), sulfo-GMBS (sGMBS), sulfo-SIAB (s-SIAB), and sulfo-MBS (s-MBS).

Preparation of the above-mentioned GnRH/mollusk hemocyanin protein conjugate is preferably conducted under conditions of approximately neutral pH and high salt concentrations to prevent the disassociation of the protein into subunits, and thereby prevent mollusk protein epitopes from being exposed to the animal's immune system. Thus, the protein is preferably dissolved in a buffer having an NaCl concentration greater than or equal to about 0.6 M, particularly about 0.9 M. Addition of sucrose to the carrier protein solution is also preferred to reduce the denaturation of the protein during freeze lyophilization processing and to allow the material to be rehydrated without precipitation. A detailed description of the conjugation procedure is provided in Example 2.

The GnRH or GnRH analog carrier conjugate is formulated with the adjuvant of the invention in the same manner described above for any immunogen of interest. However, when using compositions which include a mollusk hemocyanin carrier protein, the vaccine composition will preferably further include physiologically buffered saline with a high salt concentration to prevent dissociation of the protein. The salt (NaCl) concentration of the vaccine composition is preferably greater than or equal to about 0.7 M and less than or equal to about 1.0 M, and the pH of said vaccine composition is between about 7.0 and 8.0, with 7.4 being preferred.

In this preferred embodiment, the invention provides a method for inducing anti-GnRH antibody by administering to a subject animal a vaccine composition including the adjuvant containing killed cells of *M. avium* subsp. *avium* with the GnRH or GnRH analog conjugate. As noted, the production of the anti-GnRH antibodies effects the neutralization of GnRH in the animal, thereby reducing LH and FSH blood levels and inhibiting the production of androgens and other steroids and sperm in the testes of males, and inhibiting the production of progestogens and oestrogens and follicle maturation in the ovary of females. As a consequence, the induction of anti-GnRH antibodies may be used for effecting one or more treatments of animals, including the contraception of males and/or females, reducing aggressive behavior in male animals, chemical castration, control or prevention of estrus or heat, prevention of restlessness in animals prior to slaughter, reduction of boar taint in the meat of pigs raised for slaughter, and treatment of various diseases as noted hereinabove.

Accordingly, the GnRH or GnRH analog conjugate should be administered in an amount effective to induce one or more of these responses as determined by routine testing. For example, where the desired effect is contraception, an "effective amount" is defined to mean those quantities which will result in a significant reduction in fertility relative to an untreated control animal. Infertility can be measured by methods known in the art, e.g. by evaluation of spermatogenesis or ovulation, as well as by statistical modeling of experimental animal data. Other indicators of infertility in males includes reduction of serum testosterone to castration levels and involution of the testes. Similarly, where the ultimate response is a reduction of aggressive behavior in male animals, an effective amount is defined to mean those quantities which will result in a significant reduction in aggressive behavior of a test group as compared to an untreated group. The actual effective amount will of course vary with the specific GnRH or GnRH analog, the immunogenic carrier and manner of conjugation, the target animal and its size, the desired effect, and the treatment regimen (i.e., treatment with only a single dose, or treatment with a first dose followed by a boost dose), and may be readily determined empirically by the practitioner skilled in the art using an antigen dose response assay for each animal species.

Without being limited thereto, typical single shot doses of the GnRH or GnRH analog conjugate in the vaccine for the treatment of small animals (such as rodents, Norway rats, squirrels, rabbits, dogs, and domestic cats) will be between about 50 and 250 μg, for medium size animals (such as pigs or deer) will be between about 400 and 800 μg, and for large animals (such as cattle, bison, horses, or elk) will be between about 1,000 to 2,000 μg conjugate. The doses presented above are provided only as a guide for adult or full-size animals, and for animals encompassing a number of species or breeds, such as dogs, deer, or horses, the indicated dose is for the average or typical size animal, not "miniature" breeds or species. It is envisioned that doses for very large animals such as elephants would be considerably greater, and should be determined empirically.

We have discovered that when the vaccine is formulated with the killed *M. avium* subsp. *avium* adjuvant of this invention, the above-described doses of GnRH or GnRH analog provide effective immunocontraception for an extended period of time, eliciting high anti-GnRH antibody titers for periods of more than 1 year, after only a single dose or shot. For treatment programs utilizing two doses, a first primary dose and a second boost dose, the doses described above for a single dose regimen should be cut approximately in half for each dose.

The GnRH or GnRH analog containing vaccine of this invention are effective for treatment of a broad spectrum of both wild and domesticated animals, ranging from pets, to large domestic or wild animals, including mammals, birds, and reptiles. Without being limited thereto, preferred animals which may be treated include porcine, bovine, equine, feline, canine, primates (including humans), Rodentia, Cervidae, and Pachydermata, and particularly domestic dogs, domestic cats, pigs (including captive or feral pigs), cattle, deer, horses, zoo animals, elephants, rodents (including rats, rabbits, and squirrels), and reptiles.

The vaccine may be administered to the subject animal by parenteral injection (e.g., subcutaneous, intravenous, or intramuscular). For immunocontraceptive treatments, the vaccine should be administered prior to the desired onset of infertility to allow development of effective levels of anti-GnRH antibodies in the subject animal. Thus, the vaccine will typically be injected at least about 3 months prior to the desired time of contraception.

The following examples are intended only to further illustrate the invention and are not intended to limit the scope of the invention which is defined by the claims.

Example 1

Preparation of Adjuvant

Killed cells of *Mycobacterium avium* subsp. *avium* were obtained from the commercial Johne's disease vaccine, a *Mycobacterium avium* bacterin (provided by Solvay Animal Health Products Inc., Mendota Heights, Minn. 55120, Product # 09149). Each vial contains a total of 25.5 mg killed cells of *Mycobacterium avium* (dry weight) in 0.5 ml of mineral oil. Vials are stored at refrigerator temperature, 36 to 45° F.

A mineral oil diluent is used for preparation of the adjuvant. In a sterile 50 ml centrifuge tube, combine mineral oil (light white oil) and mannide monooleate (9:1 by weight) and vortex to mix. Store at room temperature in the sterile 50 ml vial.

A concentrated stock solution of the killed cells in mineral oil may be prepared for storage and subsequent preparation of adjuvant doses in vaccine formulations. The Stock Solution is a 1/30 dilution of the original *Mycobacterium avium* bacterin. Prepare in a sterile 50 ml centrifuge tube. Add an entire vial (0.5 ml) of *Mycobacterium avium* bacterin to 10 ml of the diluent. Rinse the *Mycobacterium avium* bacterin vial 2 times with 1 ml of diluent; each rinse is added to the 50 ml vial bringing the total volume to 12.5 ml, then add an additional 2.5 ml of diluent to the stock vial bringing the total volume to 15 ml. Vortex to mix. Vials are stored at refrigerator temperature. The concentration of killed cells in the stock solution is 1.7 mg/ml.

The stock solution is diluted as necessary to prepare both the prime and the boost dose adjuvants used in the vaccines. The primary dose adjuvant is a 1/150 dilution of original *Mycobacterium avium* bacterin. In a sterile 50 ml centrifuge tube, make a 1/5 dilution of the stock solution with the diluent. Add 1 ml of the Stock Solution to 4.0 ml of the diluent. Vortex to mix. The concentration of killed cells in the prime dose adjuvant is 340 μg/ml. Vials are stored at refrigerator temperature.

The boost dose Adjuvant is a 1/300 dilution of the *Mycobacterium avium* bacterin. In a sterile 50 ml centrifuge tube, make a 1/10 dilution of the stock solution with the diluent. Add 1 ml of the stock solution to 9.0 ml of the diluent. Vortex to mix. The concentration of killed cells in the prime dose adjuvant is 170 μg/ml. Vials are stored at refrigerator temperature.

Example 2

GnRH-KLH Vaccine Preparation

Preparation of MSB Buffer:
Add 7 tablets of Sigma Phosphate Buffered Saline (PBS) tablets to 200 ml distilled $H_2O$, to give a 0.07 M Phosphate buffer at pH 7.4 with 0.96 M NaCl. Add 5.6 gm Sucrose (41 mM Sucrose) to the PBS solution. For long term stability the buffer is frozen. MSB is stable for about 30 days in refrigerator.

Preparation of GnRH/KLH Conjugate:
KLH carrier protein is first subjected to maleimide activation for addition of sulfide binging groups thereto. 10 mg of the mollusk protein KLH is dissolved in the MSB buffer, and 2 mg of sulfo-SMCC is added (Pierce Chemical Co.) with gentle mixing to dissolve. The mixture is allowed to react for 1 hour at room temperature with periodic mixing. After completion of the reaction, the maleimide-activated protein is immediately purified by applying the reaction mixture to a desalting column (i.e., Sephadex G-25). The maleimide activated protein comes off on the void volume (first peak, fractions 4-6) as measured by absorbance at 280 nm. There is a drop in absorbance after fraction 6, and a rise in absorbance in fractions 7 or 8 as the excess sulfo-SMCC comes off. Excess cross-linker is removed in order to achieve good conjugation to the hapten. At this point the maleimide activated KLH may be frozen or freeze dried.

GnRH Hapten Conjugation:
Six mg of the GnRH-Gly-Cys hapten (containing an free SH on one end) is dissolved in 1 ml of $H_2O$. The dissolved hapten is added to the activated KLH and allowed to react for 2 hours at room temperature and then overnight in the refrigerator. The KLH-hapten conjugate is immediately purified by applying the reaction mixture to a desalting column. (Sephadex G-25). The conjugate protein should come off on the void volume (first peak, fractions 4-6) as measure by absorbance at 280 nm. There should be a drop in absorbance after fraction 6 and rise in absorbance in fractions 7 or 8 as the excess hapten comes off. A small amount of excess hapten does not cause problem in a prime dose but could neutralize antibody in a boost dose if it is present in large excess. The GnRH/KLH conjugate may be frozen or lyophilized or used in the present form.

GnRH Vaccine Formulation:
Primary dose formulations of the vaccine are prepared by mixing equal portions (1:1 ratio) of GnRH-KLH conjugate (0.5 ml) with the prime dose adjuvant of Example 1 (1/150) (0.5 ml). The final vaccine dose should contain approximately 170 μg of killed bacteria per 0.5 ml dose. The GnRH conjugate must be added to the oil adjuvant (not oil to GnRH) in a drop wise manner while the oil is vortexed. This forms a milk like emulsion. The emulsion is stiffened by passing through a 22 gauge needle 3 times.

Boost dose formulations of the vaccine are prepared by mixing equal portions (1:1 ratio) of GnRH-KLH vaccine (0.5 ml) with the boost dose adjuvant of Example 1 (1/300) (0.5 ml). The final vaccine dose should contain approximately 85 μg of killed bacteria per 0.5 ml dose. Again, the GnRH conjugate must be added to the oil adjuvant (not oil to GnRH) in a drop wise manner while the oil is vortexed. This forms a milk like emulsion. The emulsion is stiffened by passing through a 22 gauge needle 3 times.

Example 3

Immunocontraception of Deer

The GnRH immunocontraceptive vaccine of Example 2 was used for the immunocontraception of deer as either a two shot or single shot vaccine.

Two Shot Trial:
Deer were injected with a first, prime boost, followed by injection 1 year later with a second, boost injection of the GnRH/adjuvant vaccines of Example 1. The deer were injected with 1 ml of the vaccine composition. Titers of anti-GnRH antibodies and blood progesterone levels were monitored over a two year period immediately prior to and following treatment. The amount of the conjugate in each dose of the vaccine was 450 μg.

The results are shown in FIG. 1. Deer injected with a prime and boost vaccination of KLH-GnRH/Adjuvant in the breeding season of the first year of the trial have remained infertile through four consecutive breeding seasons (four years) without a second or third season boost vaccine. Anti-GnRH antibody titers remained at 128,000 into the third year, and dropped to 28,000 in the fourth year with deer remaining infertile (FIG. 1). The two shot paradigm effectively contracepted deer from 2 to 4 years. Two out of the 3 deer tested were still infertile after 4 years.

Figure 2:
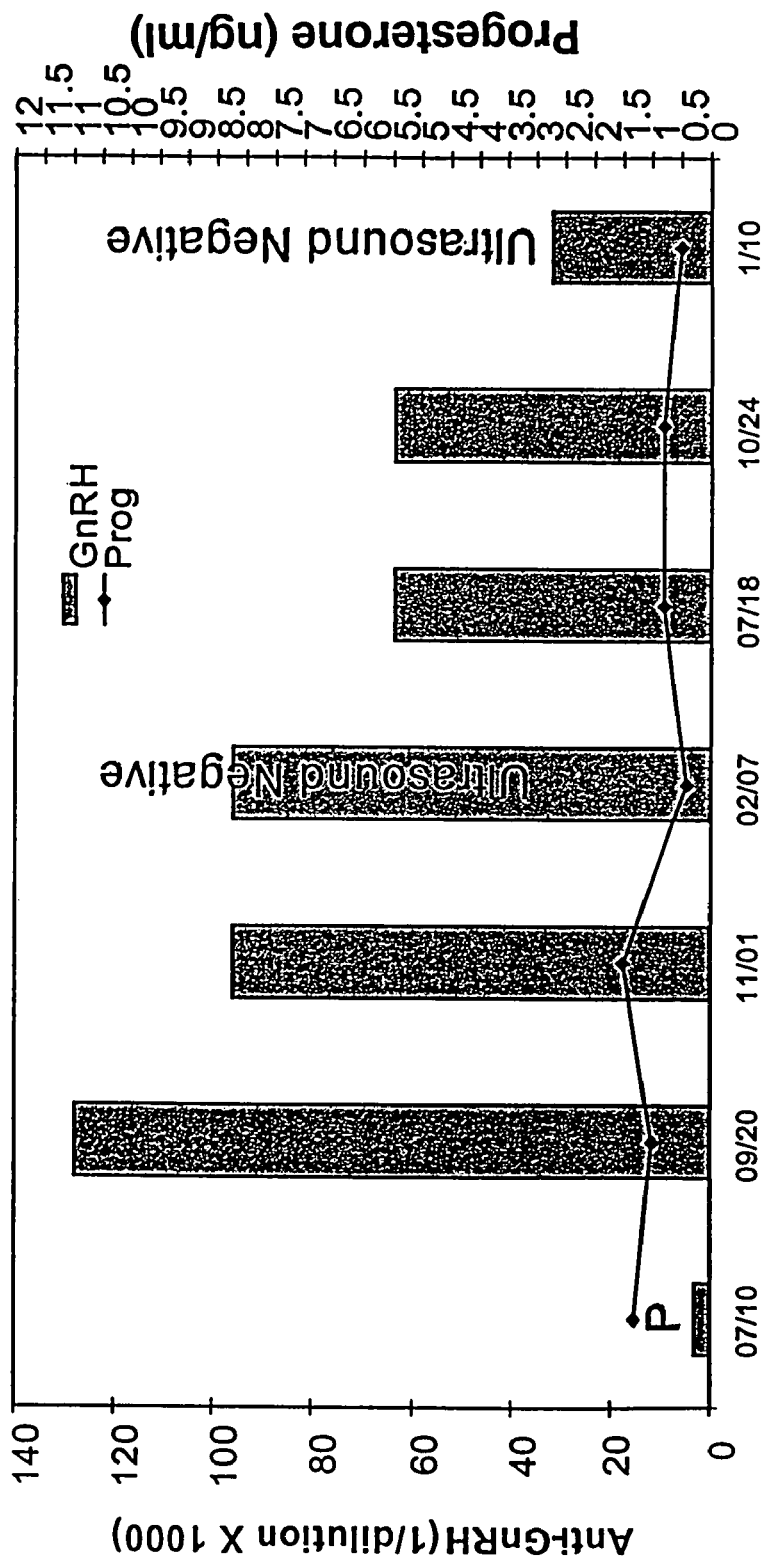
FIG. 2 shows the results of the second study of Example 3 over two seasons with female deer using only a single shot of the vaccine.

One Shot Trial with Female Deer:

Following the success observed after two mating seasons of the two shot trial, a second trial was commenced to determine efficacy using only a single shot of the vaccine of Example 2. In July prior to the first mating season of this single shot trial, 5 Penn State deer were injected with 1 ml of the vaccine composition. The dose of the GnRH conjugate was increased over that used in the two shot trial; the concentration of the GnRH concentration was 850 μg/ml. They were exposed to the bucks on November of that year. All five remained infertile for that year. FIG. 2 represents a typical antibody response for the single shot deer. In the 2nd year 3 out of the 5 remained infertile, while two of the deer had a single fawn indicating a partial protection.

Single Shot Trial with Male Deer:

One season after the single shot trial was initiated with female deer, male deer were subjected to a single shot trial. In July prior to the first mating season of this trial, 5 male deer were injected with a single shot GnRH using the same amounts and concentrations of vaccine as in the single shot trial with the females (1 ml dose containing 850 μg of conjugate). In the November bleed the testosterone levels of all 5 deer were down to the level of sexually immature deer, and their antlers had prematurely dropped off. Therefore the single shot regimen was effective in shutting the sexual activity of all male and female deer for at least one year (Table 1).

Example 4

Immunocontraception of Pigs

The GnRH immunocontraceptive vaccine of Example 2 was used for the immunocontraception of pigs as a single shot vaccine.

Figure 3:
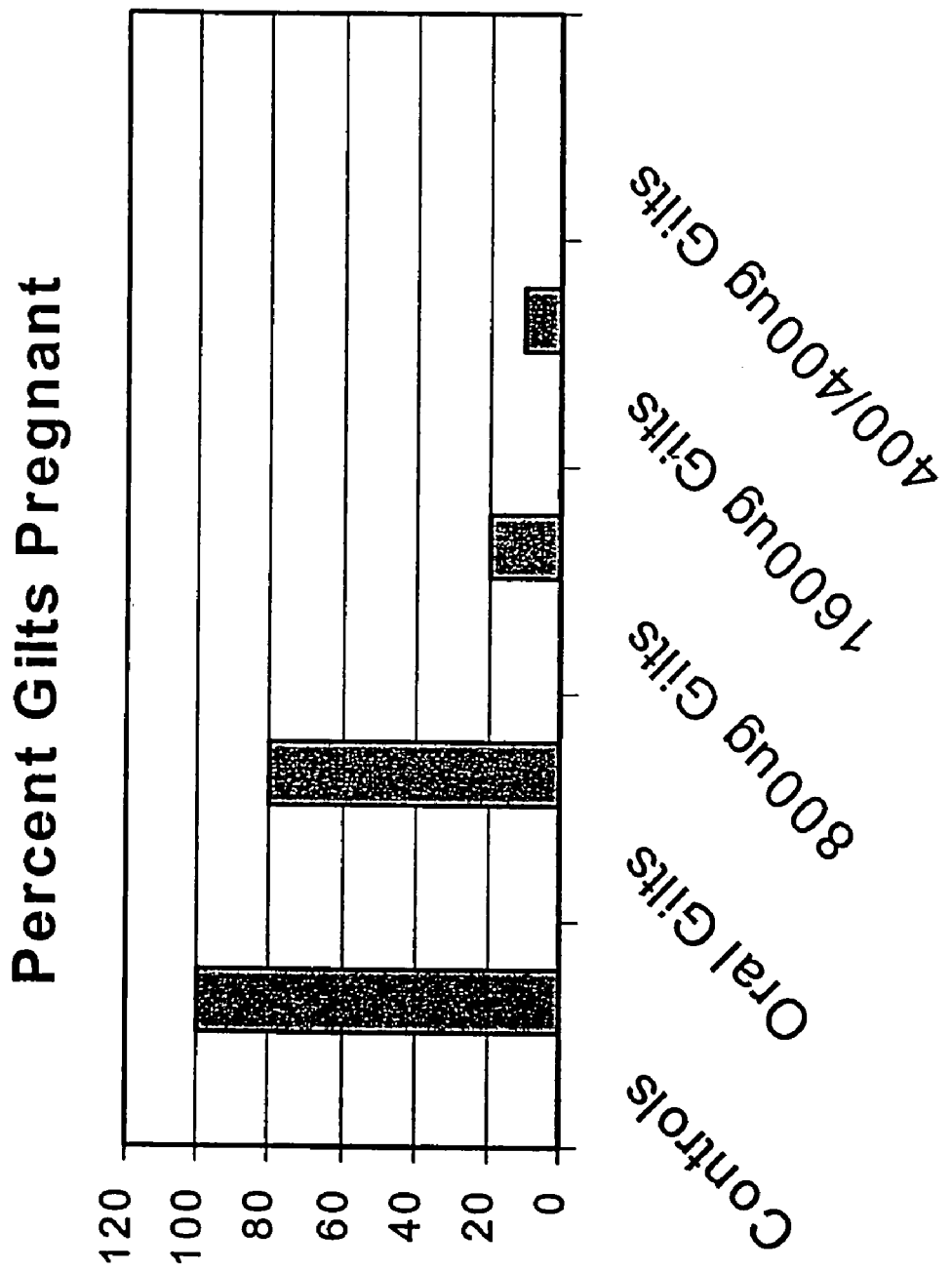
FIG. 3 shows the results of the study of Example 4 with female pigs.

The GnRH/adjuvant vaccine was tested in fifty 5 month old gilts. Pigs of Group 1 (n=10) were sham injected with the adjuvant only, while pigs of Group 2 (n=10) were given 2 oral doses of GnRH on mixed nut shells, Group 3 (n=10) were given a single dose containing 800 μg of GnRH conjugate, Group 4 (n=10) were given a single dose of 1600 μg of GnRH conjugate, and Group 5 (n=10) were given 2 doses of 400 μg of GnRH conjugate 30 days apart. At eight months of age or 3 months after the contraceptive vaccine was given the gilts were checked for heat by teasing with a boar. The results which are dose related are shown in FIG. 3. The 2 dose trial was the most effective giving a 100% contraceptive effect. However, the high single dose gave 90% contraceptive effect response.

Figures 4A, 4B:
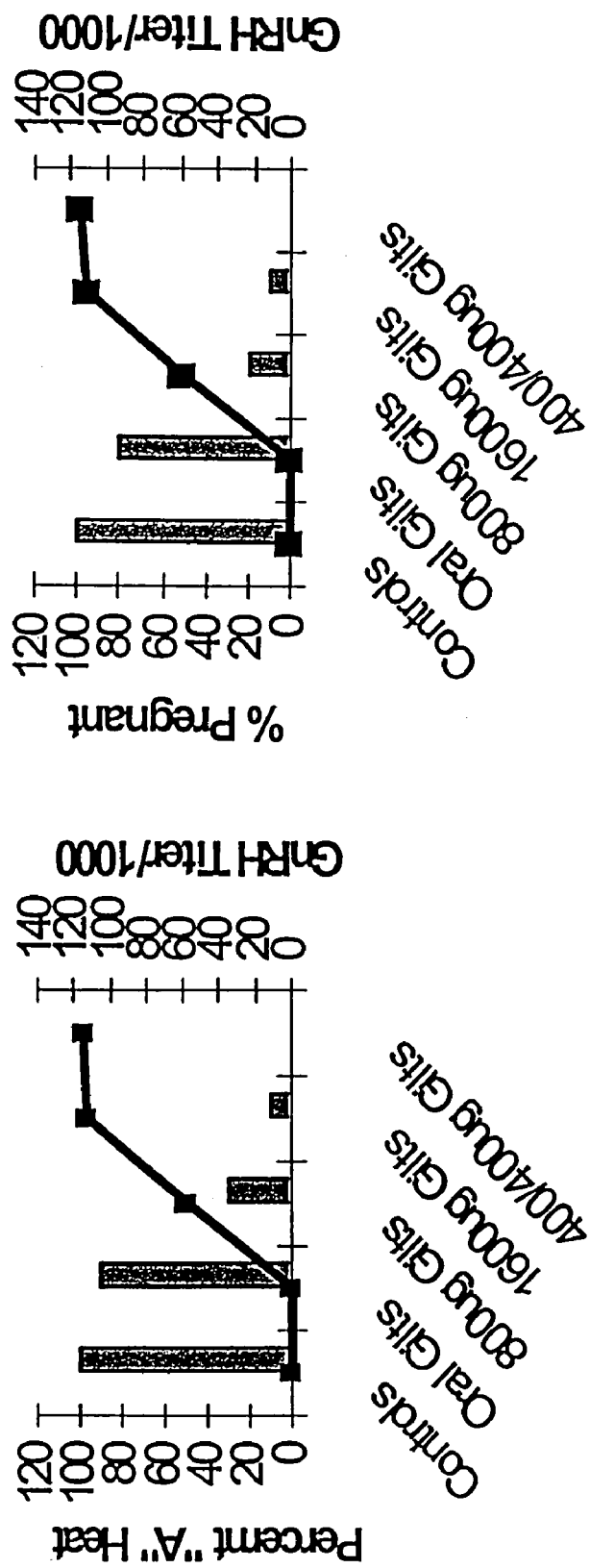
FIGS. 4(a) and 4(b) shows the results of the study of Example 4 with female pigs.

As seen in FIG. 4 the heat cycles and pregnancy observed in the 8 months old female gilt decreased as the GnRH antibody titer increased.

It is understood that the foregoing detailed description is given merely by way of illustration and that modifications and variations may be made therein without departing from the spirit and scope of the invention.

TABLE 1

| | White Tailed Bucks Single Shot | | | |
|---|---|---|---|---|
| | Anti-GnRH | Testosterone (ng/dl) | Testis (μm) | Antlers |
| Control | 0 ± 0 | 477 ± 172 | 73 × 43 | hardened |
| One Shot regimen | 48K ± 23K | 4 ± 6 | 44 × 28 | velvet or shed |

---

We claim:

1. A method for immunocontraception of an animal which comprises administering an immunocontraceptive vaccine composition to said animal which comprises:
   a. an immunogen comprising GnRH or a GnRH immunogenic analog conjugated to a carrier protein, wherein said immunogen is provided in an amount effective for inducing immunocontraception of said animal in a single dose, and
   b. an adjuvant comprising mineral oil and killed cells of *Mycobacterium avium* subspecies *avium*, the concentration of said killed cells of *Mycobacterium avium* being greater than or equal to about 50 µg per ml and less than or equal to about 400 µg per ml, measured as the dry weight of said killed cells per ml of said vaccine composition;
   wherein said vaccine composition is administered in a single dose, without a second or boost dose, for a period of at least one year.

2. The method of claim 1 wherein the amount of said killed cells of *Mycobacterium avium* subspecies *avium* in said vaccine composition is less than or equal to about 400 µg, measured as the dry weight of said killed cells.

3. The method of claim 2 wherein the amount of said killed cells of *Mycobacterium avium* subspecies *avium* in said vaccine composition is less than or equal to about 200 µg, measured as the dry weight of said killed cells.

4. The method of claim 1 wherein said animal is selected from the group consisting of porcine, bovine, equine, feline, canine, primates, Rodentia, Cervidae, and Pachydermata.

5. The method of claim 1 wherein said animal is selected from the group consisting of domestic dogs, domestic cats, pigs, cattle, deer, horses, zoo animals, elephants, rodents, and reptiles.

6. The method of claim 1 wherein said adjuvant further comprises a surfactant.

7. The method of claim 1 wherein said immunogen comprises GnRH or a GnRH immunogenic analog conjugated to KLH carrier protein, and said GnRH or GnRH immunogenic analog is conjugated to said KLH carrier protein through the C-terminal end of said GnRH or GnRH immunogenic analog.

8. The method of claim 7 wherein said vaccine composition further comprises physiologically buffered saline, and further wherein the salt concentration of said vaccine composition is greater than or equal to about 0.7 M and less than or equal to about 1.0 M, and the pH of said vaccine composition is between about 7.0 and 8.0.

9. The method of claim 1 wherein said vaccine composition is administered by parenteral injection.

10. The method of claim 1 wherein the amount of said killed cells of *Mycobacterium avium* in said vaccine composition is not sufficient to elicit a substantial T cell-mediated delayed hypersensitivity response to *M. avium* by said animal if said adjuvant was administered alone, without said immunogen.

11. The method of claim 1 wherein said animal is selected from the group consisting of deer, domestic cats, squirrels, horses, and elk.

* * * * *

SEQUENCE LISTING

<160> NUMBER OF SEQ ID NOS: 21

<210> SEQ ID NO 1
<211> LENGTH: 10
<212> TYPE: PRT
<213> ORGANISM: mammalian
<220> FEATURE:
<221> NAME/KEY: VARIANT
<222> LOCATION: (1)
<223> OTHER INFORMATION: Xaa = pGlu (pyroglutamic acid or pyrrolidone
      carboxylic acid)

<400> SEQUENCE: 1

Xaa His Trp Ser Tyr Gly Leu Arg Pro Gly
 1               5                  10

<210> SEQ ID NO 2
<211> LENGTH: 10
<212> TYPE: PRT
<213> ORGANISM: mammalian
<220> FEATURE:
<221> NAME/KEY: VARIANT
<222> LOCATION: (1)
<223> OTHER INFORMATION: Xaa = pGlu (pyroglutamic acid or pyrrolidone
      carboxylic acid)

<400> SEQUENCE: 2

Xaa His Trp Ser Tyr Trp Leu Arg Pro Gly
 1               5                   10

<210> SEQ ID NO 3
<211> LENGTH: 10
<212> TYPE: PRT
<213> ORGANISM: mammalian
<220> FEATURE:
<221> NAME/KEY: VARIANT
<222> LOCATION: (1)
<223> OTHER INFORMATION: Xaa = pGlu (pyroglutamic acid or pyrrolidone
      carboxylic acid)

<400> SEQUENCE: 3

Xaa His Trp Ser Tyr Glu Leu Arg Pro Gly
 1               5                   10

<210> SEQ ID NO 4
<211> LENGTH: 10
<212> TYPE: PRT
<213> ORGANISM: mammalian
<220> FEATURE:
<221> NAME/KEY: VARIANT
<222> LOCATION: (1)
<223> OTHER INFORMATION: Xaa = pGlu (pyroglutamic acid or pyrrolidone
      carboxylic acid)

<400> SEQUENCE: 4

Xaa His Trp Ser Tyr Lys Leu Arg Pro Gly
 1               5                   10

<210> SEQ ID NO 5
<211> LENGTH: 10
<212> TYPE: PRT
<213> ORGANISM: mammalian

<400> SEQUENCE: 5

Glu His Trp Ser Tyr Gly Leu Arg Pro Gly
 1               5                   10

<210> SEQ ID NO 6
<211> LENGTH: 10
<212> TYPE: PRT
<213> ORGANISM: mammalian

<400> SEQUENCE: 6

His His Trp Ser Tyr Gly Leu Arg Pro Gly
 1               5                   10

<210> SEQ ID NO 7
<211> LENGTH: 10
<212> TYPE: PRT
<213> ORGANISM: mammalian

<400> SEQUENCE: 7

Pro His Trp Ser Tyr Gly Leu Arg Pro Gly
 1               5                   10

<210> SEQ ID NO 8
<211> LENGTH: 5
<212> TYPE: PRT
<213> ORGANISM: mammalian
<220> FEATURE:
<221> NAME/KEY: VARIANT
<222> LOCATION: (1)
<223> OTHER INFORMATION: Xaa = pGlu (pyroglutamic acid or pyrrolidone
      carboxylic acid)

```
<400> SEQUENCE: 8

Xaa His Trp Ser Tyr
 1               5

<210> SEQ ID NO 9
<211> LENGTH: 6
<212> TYPE: PRT
<213> ORGANISM: mammalian
<220> FEATURE:
<221> NAME/KEY: VARIANT
<222> LOCATION: (1)
<223> OTHER INFORMATION: Xaa = pGlu (pyroglutamic acid or pyrrolidone
      carboxylic acid)

<400> SEQUENCE: 9

Xaa His Trp Ser Tyr Gly
 1               5

<210> SEQ ID NO 10
<211> LENGTH: 7
<212> TYPE: PRT
<213> ORGANISM: mammalian
<220> FEATURE:
<221> NAME/KEY: VARIANT
<222> LOCATION: (1)
<223> OTHER INFORMATION: Xaa = pGlu (pyroglutamic acid or pyrrolidone
      carboxylic acid)

<400> SEQUENCE: 10

Xaa His Trp Ser Tyr Gly Leu
 1               5

<210> SEQ ID NO 11
<211> LENGTH: 7
<212> TYPE: PRT
<213> ORGANISM: mammalian

<400> SEQUENCE: 11

His Trp Ser Tyr Gly Leu Arg
 1               5

<210> SEQ ID NO 12
<211> LENGTH: 6
<212> TYPE: PRT
<213> ORGANISM: mammalian

<400> SEQUENCE: 12

Trp Ser Tyr Gly Leu Arg
 1               5

<210> SEQ ID NO 13
<211> LENGTH: 7
<212> TYPE: PRT
<213> ORGANISM: mammalian

<400> SEQUENCE: 13

Ser Tyr Gly Leu Arg Pro Gly
 1               5

<210> SEQ ID NO 14
<211> LENGTH: 6
<212> TYPE: PRT
<213> ORGANISM: mammalian

<400> SEQUENCE: 14
```

```
Tyr Gly Leu Arg Pro Gly
  1               5

<210> SEQ ID NO 15
<211> LENGTH: 10
<212> TYPE: PRT
<213> ORGANISM: Gallus gallus
<220> FEATURE:
<221> NAME/KEY: VARIANT
<222> LOCATION: (1)
<223> OTHER INFORMATION: Xaa = pGlu (pyroglutamic acid or pyrrolidone
      carboxylic acid)

<400> SEQUENCE: 15

Xaa His Trp Ser His Gly Trp Tyr Pro Gly
  1               5                  10

<210> SEQ ID NO 16
<211> LENGTH: 10
<212> TYPE: PRT
<213> ORGANISM: Salmo sp.
<220> FEATURE:
<221> NAME/KEY: VARIANT
<222> LOCATION: (1)
<223> OTHER INFORMATION: Xaa = pGlu (pyroglutamic acid or pyrrolidone
      carboxylic acid)

<400> SEQUENCE: 16

Xaa His Trp Ser Tyr Gly Trp Leu Pro Gly
  1               5                  10

<210> SEQ ID NO 17
<211> LENGTH: 9
<212> TYPE: PRT
<213> ORGANISM: mammalian

<400> SEQUENCE: 17

Lys Trp Ser Tyr Gly Leu Arg Pro Gly
  1               5

<210> SEQ ID NO 18
<211> LENGTH: 10
<212> TYPE: PRT
<213> ORGANISM: mammalian

<400> SEQUENCE: 18

Cys Lys Trp Ser Tyr Gly Leu Arg Pro Gly
  1               5                  10

<210> SEQ ID NO 19
<211> LENGTH: 20
<212> TYPE: PRT
<213> ORGANISM: mammalian

<400> SEQUENCE: 19

Gly Pro Arg Leu Gly Tyr Ser Trp Lys Cys Cys Lys Trp Ser Tyr Gly
  1               5                  10                  15

Leu Arg Pro Gly
             20

<210> SEQ ID NO 20
<211> LENGTH: 20
<212> TYPE: PRT
<213> ORGANISM: mammalian
<220> FEATURE:
<221> NAME/KEY: VARIANT
<222> LOCATION: (1)
```

```
-continued

<223> OTHER INFORMATION: Xaa = pGlu (pyroglutamic acid or pyrrolidone
      carboxylic acid) or Gln

<400> SEQUENCE: 20

Xaa His Trp Ser Tyr Gly Leu Arg Pro Gly Gln His Trp Ser Tyr Gly
 1               5                  10                  15

Leu Arg Pro Gly
            20

<210> SEQ ID NO 21
<211> LENGTH: 21
<212> TYPE: PRT
<213> ORGANISM: mammalian
<220> FEATURE:
<221> NAME/KEY: VARIANT
<222> LOCATION: (1)
<223> OTHER INFORMATION: Xaa = pGlu (pyroglutamic acid or pyrrolidone
      carboxylic acid)
<220> FEATURE:
<221> NAME/KEY: VARIANT
<222> LOCATION: (6)
<223> OTHER INFORMATION: Xaa = Gly or D-amino acid which may optionally
      contain an amino acid side chain
<220> FEATURE:
<221> NAME/KEY: VARIANT
<222> LOCATION: (16)
<223> OTHER INFORMATION: Xaa = Gly or D-amino acid which may optionally
      contain an amino acid side chain

<400> SEQUENCE: 21

Xaa His Trp Ser Tyr Xaa Leu Arg Pro Gly Gln His Trp Ser Tyr Xaa
 1               5                  10                  15

Leu Arg Pro Gly Cys
            20
```